United States Patent
Baruch et al.

(10) Patent No.: US 6,723,054 B1
(45) Date of Patent: Apr. 20, 2004

(54) APPARATUS AND METHOD FOR MEASURING PULSE TRANSIT TIME

(75) Inventors: Martin C. Baruch, Charlottesville, VA (US); David W. Gerdt, Charlottesville, VA (US); Charles Adkins, Earlysville, VA (US)

(73) Assignee: Empirical Technologies Corporation, Charlottesville, VA (US)

( * ) Notice: Subject to any disclaimer, the term of this patent is extended or adjusted under 35 U.S.C. 154(b) by 0 days.

(21) Appl. No.: 09/763,657

(22) PCT Filed: Aug. 24, 1999

(86) PCT No.: PCT/US99/19258

§ 371 (c)(1),
(2), (4) Date: Feb. 26, 2001

(87) PCT Pub. No.: WO00/10453

PCT Pub. Date: Mar. 2, 2000

Related U.S. Application Data

(60) Provisional application No. 60/097,618, filed on Aug. 24, 1998, and provisional application No. 60/126,339, filed on Mar. 26, 1999.

(51) Int. Cl.[7] ............................... A61B 5/02; A61B 5/00
(52) U.S. Cl. ....................... 600/500; 600/485; 600/481; 600/342
(58) Field of Search ................................ 600/485, 481, 600/486, 500, 501, 502, 503, 310, 342

(56) References Cited

U.S. PATENT DOCUMENTS

| | | | |
|---|---|---|---|
| 4,245,648 A | 1/1981 | Trimmer et al. | 128/680 |
| 4,545,253 A | 10/1985 | Avicola | 73/655 |
| 4,634,858 A | 1/1987 | Gerdt et al. | |
| 4,752,141 A | 6/1988 | Sun et al. | |
| 4,763,977 A | 8/1988 | Kawasaki et al. | 350/96.15 |
| 4,862,144 A | 8/1989 | Tao | |

(List continued on next page.)

OTHER PUBLICATIONS

Tatterson, Kathleen G., "Optical Acoustic Sensors Could Aid Diagnoses", Photonics Spectra, Oct. 1997, pp. 55–56.

*Primary Examiner*—Max F. Hindenburg
*Assistant Examiner*—Navin Natnithithadha
(74) *Attorney, Agent, or Firm*—Miles & Stockbridge P.C.

(57) ABSTRACT

In a method of measuring pulse transit time of a living subject, first and second pulse wave signals are produced by sensing the pulse at first and second pulse points, respectively, the first and second pulse points being spaced from one another. The first and second pulse wave signals are differentiated, and based on the results, corresponding points of the first and second pulse wave signals are selected (e.g., points of maximum slope). The time delay between the selected points is determined, thus yielding the pulse transit time. A preferred apparatus measures pulse transit time using at least one fiberoptic pulse sensor including a fused-fiber coupling region having at least a portion that can be deflected without putting the coupling region under tension.

24 Claims, 14 Drawing Sheets

U.S. PATENT DOCUMENTS

| | | |
|---|---|---|
| 4,947,859 A | 8/1990 | Brewer et al. ............... 128/715 |
| 5,026,984 A | 6/1991 | Gerdt |
| 5,056,884 A | 10/1991 | Quinlan, Jr. |
| 5,074,309 A | 12/1991 | Gerdt |
| 5,136,669 A | 8/1992 | Gerdt |
| 5,173,747 A | 12/1992 | Boiarski et al. ............ 356/361 |
| 5,187,366 A | 2/1993 | Hopenfeld ................. 250/302 |
| 5,200,615 A | 4/1993 | Hopenfeld ................. 250/302 |
| 5,222,165 A | 6/1993 | Bohlinger |
| 5,289,256 A | 2/1994 | Gramling ................... 356/345 |
| 5,303,586 A | 4/1994 | Zhao et al. .................. 73/293 |
| 5,333,217 A | 7/1994 | Kossat ........................ 385/32 |
| 5,339,374 A | 8/1994 | Murphy et al. |
| 5,340,715 A | 8/1994 | Slovacek et al. ............. 435/6 |
| 5,343,037 A | 8/1994 | Berkcan ............... 250/227.21 |
| 5,362,971 A | 11/1994 | McMahon et al. .......... 250/577 |
| 5,378,889 A | 1/1995 | Lawrence .............. 250/227.16 |
| 5,394,239 A | 2/1995 | Valette ....................... 356/345 |
| 5,481,922 A | 1/1996 | Washabaugh ................ 73/774 |
| 5,494,798 A | 2/1996 | Gerdt et al. |
| 5,525,800 A | 6/1996 | Sanghera et al. ...... 250/339.08 |
| 5,532,493 A | 7/1996 | Hale et al. ................ 250/458.1 |
| 5,535,747 A | 7/1996 | Katakura et al. ...... 128/660.02 |
| 5,649,543 A | 7/1997 | Hosaka et al. |
| 5,671,191 A | 9/1997 | Gerdt |
| 5,684,460 A | 11/1997 | Scanlon ...................... 340/573 |
| 5,699,461 A | 12/1997 | Minemoto et al. |
| 5,712,934 A | 1/1998 | Johnson ...................... 385/12 |
| 5,828,798 A | 10/1998 | Hopenfeld ................. 385/12 |
| 6,331,162 B1 * | 12/2001 | Mitchell ..................... 600/485 |

\* cited by examiner

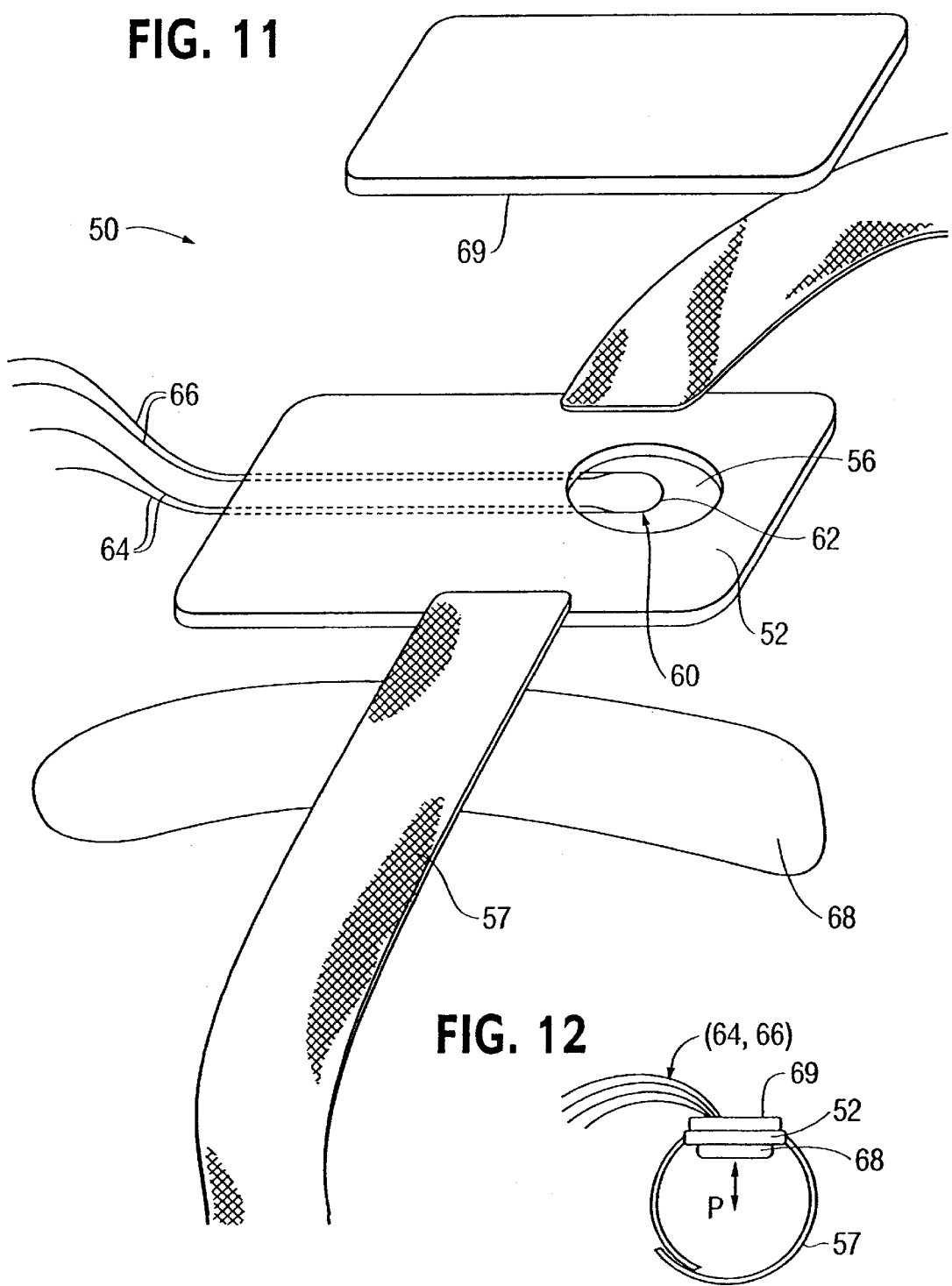

APPARATUS AND METHOD FOR MEASURING PULSE TRANSIT TIME

CROSS-REFERENCE TO RELATED APPLICATIONS

This application claims the benefit of U.S. Provisional Application Nos. 60/097,618 filed Aug. 24, 1998, and 60/126,339 filed Mar. 26, 1999, both of which are incorporated herein by reference.

BACKGROUND OF THE INVENTION

This invention relates to a method and apparatus for measuring pulse wave transmission, and more particularly pulse transit time, of a human or mammalian subject.

The human (or mammalian) pulse is a traveling wave disturbance that emanates from the heart and travels throughout the arterial system. Since the velocity of pulse propagation in a liquid is directly proportional to the pressure of the liquid, it is possible to detect blood pressure by measuring the propagation velocity of the pulse wave. The propagation velocity of the pulse wave can be measured by detecting the pulse transit time, which is the time period required for the pulse wave to travel between two spaced arterial pulse points.

An example of a blood pressure monitoring system that utilizes pulse transit time can be found in U.S. Pat. No. 4,245,648 to Trimmer et al. This system includes a pair of piezoelectric sensors closely spaced (by about 3 cm.) along the brachial artery to detect the traveling pulse wave. Pulse transit time is determined as the difference between arrival times of the pulse wave at the two sensors.

The use of piezoelectric sensors as described in the aforementioned patent leads to several significant practical limitations. For example, piezoelectric sensors commonly exhibit limited sensitivity at frequencies below about 2 Hz. The pulse rate of a human adult is ordinarily around 60 beats per minute, or 1 Hz. The pulse rate of a human infant is typically about 120 to 180 beats per minute, or 2 to 3 Hz. Thus, the practical requirements of a system using piezoelectric sensors for monitoring human subjects may push the limit of, or even exceed, the performance capabilities of the sensors. Another practical limitation stems from the fact that piezoelectric sensors require the presence of electrically conductive material (e.g., electrodes and lead wires) at the sensor location on the test subject. The system consequently cannot be used in environments where the presence of such materials would be problematical. For example, electrically conductive materials have been known to cause severe burning of patients undergoing MRI examinations, due to the presence of strong radio frequency fields generated by the MRI machine. Still another limitation is imposed by the location of the sensors in mutual proximity along the same artery. Locating the sensors in mutual proximity means that the pulse transit time to be measured will be very short and inherently more difficult to measure accurately. It will be appreciated that a given amount of error becomes more significant as the time period being measured becomes shorter.

SUMMARY OF THE INVENTION

In one of its aspects, the present invention provides a method of measuring pulse transit time that is especially useful (although not limited to use) with pulse sensors located at substantially spaced pulse points. For example, one of the sensors may be located over the brachial artery near or on the upper arm, and the other sensor located over the radial artery on the wrist. The method involves differentiation of the respective pulse wave signals from the sensors to determine corresponding points of the two signals, such as the points of maximum slope. The time delay between these points is then determined, thus yielding the pulse transit time. Differentiating the two pulse wave signals facilitates the identification of corresponding points of the signals, even though the pulse waveforms may differ somewhat when the sensors are substantially spaced from one another as noted above. Further, it allows for the selection of a consistent time marker (e.g., point of maximum slope) upon which to base the pulse transit time calculation from one pulse wave to the next. This is particularly advantageous since the pulse waveform ordinarily varies from one heartbeat to the next.

In another of its aspects, the invention provides an apparatus for implementing the foregoing method. The apparatus includes a pair of pulse sensors and a signal processing unit that processes the respective pulse wave signals of the pulse sensors in accordance with the method.

In another of its aspects, the present invention provides an apparatus for measuring pulse transit time including at least one pulse sensor, and preferably two pulse sensors, constituted by a variable coupler fiberoptic sensor having an improved design to be described herein. The apparatus further includes a signal processor and may be used to implement the aforementioned method or to implement other methods of measuring pulse transit time.

Other aspects of the invention will become apparent from a reading of the following detailed description with reference to the accompanying drawings.

BRIEF DESCRIPTION OF THE DRAWINGS

FIG. 11 is an exploded view of another variable coupler fiberoptic sensor useful in apparatus according to the invention.

FIG. 12 is an end view of the FIG. 9 sensor in assembled form.

DETAILED DESCRIPTION OF THE INVENTION

Figure 1:
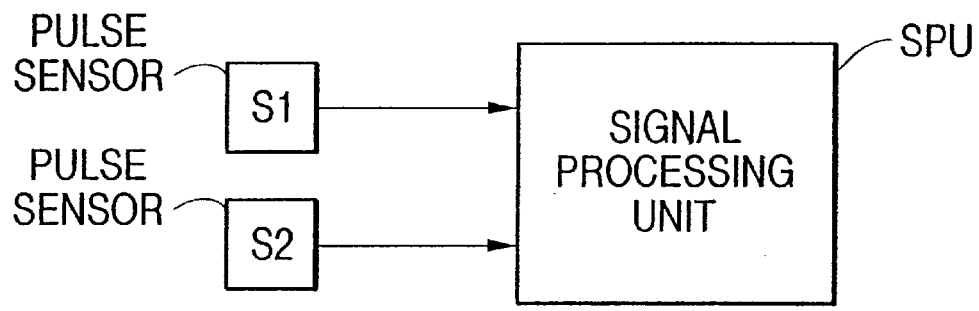
FIG. 1 is a block diagram of an apparatus for measuring pulse transit time in accordance with the invention.

FIG. 1 is a block diagram of an apparatus for measuring pulse transit time in accordance with the invention. The apparatus includes two arterial pulse sensors S1,S2 which may be of any suitable form. For example, the sensors may be piezoelectric, fiberoptic, or of any known design capable of converting skin displacements due to the pulse (pressure) wave to a corresponding output signal representative of the pulse waveform. However, at least one and preferably both of the sensors will be in the form of a variable coupler fiberoptic sensor constructed in accordance with the improved design principles to be described later.

The pulse sensors S1,S2 are connected to a signal processing unit SPU which processes the output signals from the sensors to determine the pulse transit time. The signal processing unit may be of either digital or analog design as desired. Of course, if digital processing is used, the sensor outputs may be supplied to the signal processing unit via analog-to-digital converters, or the processing unit may be provided with such converters internally.

Figure 2:
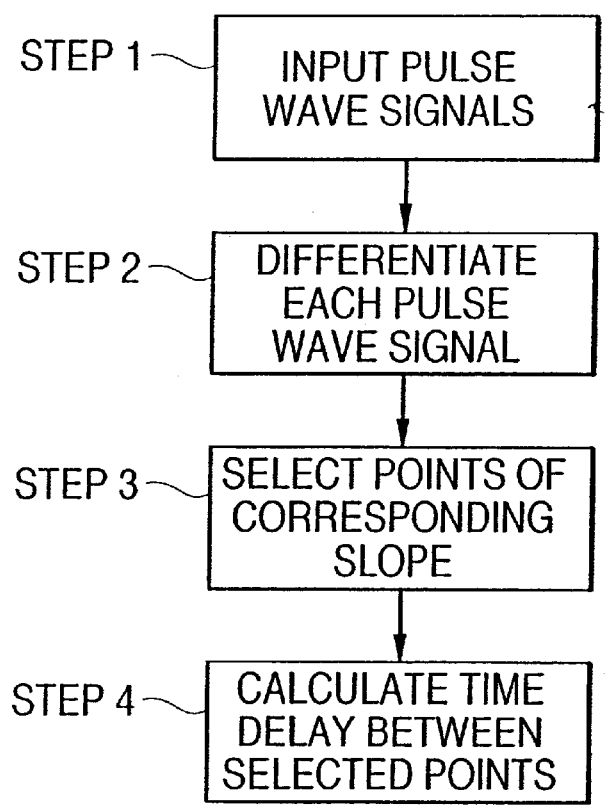
FIG. 2 is a flow diagram for explaining the operation of the system in FIG. 1.

Referring additionally to FIG. 2, the operation of the signal processing unit SPU in accordance with the invention will now be explained. At first, in Step 1, the signal processing unit inputs the pulse wave signals from sensors S1,S2. Next, in Step 2, the signal processing unit differentiates (takes the derivative of) each pulse wave signal. The derivative, of course, indicates the instantaneous slope of the pulse wave signal. Next, in Step 3, the signal processing unit uses the results of Step 2 to select points having corresponding slope characteristics from the two pulse wave signals. For example, the processing unit may select the respective points of maximum slope in the two pulse wave signals. Finally, in Step 4, the signal processing unit calculates the time delay between the two selected points. The calculated time delay constitutes the pulse transit time.

Because corresponding points of the two pulse wave signals can easily be identified from the differentiated waveforms, the foregoing method readily accommodates substantial separation of the sensors S1, S2, even though the pulse waveforms may be somewhat different at the two sensor locations. Further, as noted earlier, differentiation also allows for the selection of a consistent time marker (e.g., point of maximum slope) upon which to base the pulse transit time calculation from one pulse wave to the next. This is particularly advantageous since the pulse waveform ordinarily varies from one heartbeat to the next.

Figure 3:
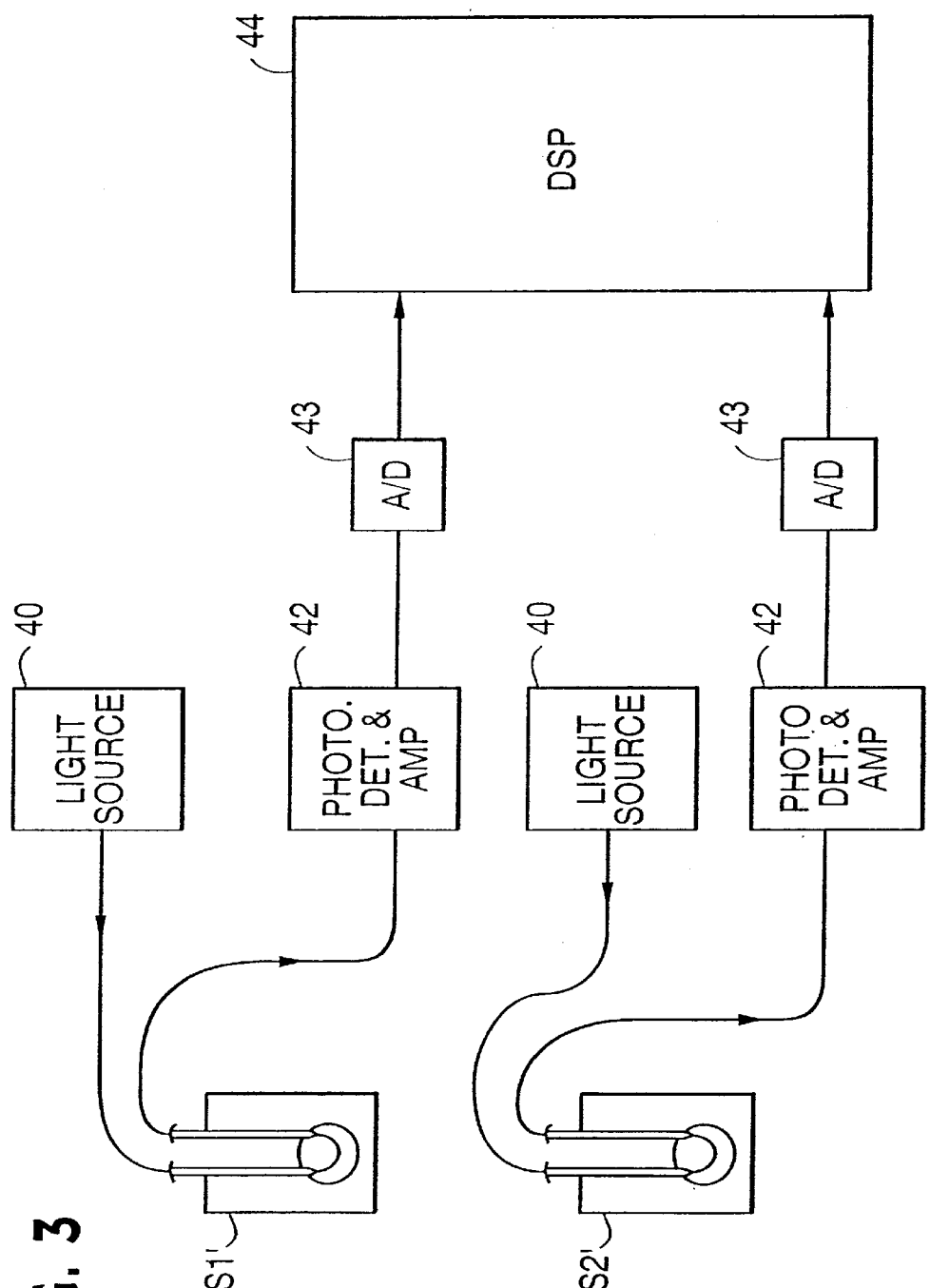
FIG. 3 is a block diagram showing another apparatus of the invention.

FIG. 3 illustrates another apparatus according to the present invention. The apparatus includes a pair of variable coupler fiberoptic sensors S1',S2' of an improved design to be explained herein. But first, in order to fully appreciate the advantages of the apparatus, some additional background regarding variable coupler fiberoptic sensors will be helpful.

Variable coupler fiberoptic sensors conventionally employ so-called biconical fused tapered couplers manufactured by a draw and fuse process in which a plurality of optical fibers are stretched (drawn) and fused together at high temperature. The plastic sheathing is first removed from each of the fibers to expose the portions for forming the fusion region. These portions are juxtaposed, usually intertwisted one to several twists, and then stretched while being maintained above their softening temperature in an electric furnace or the like. As the exposed portions of the fibers are stretched, they fuse together to form a narrowed waist region—the fusion region—that is capable of coupling light between the fibers. During the stretching process, light is injected into an input end of one of the fibers and monitored at the output ends of each of the fibers to determine the coupling ratio. The coupling ratio changes with the length of the waist region, and the fibers are stretched until the desired coupling ratio is achieved, typically by a stretching amount at which the respective fiber light outputs are equal. The coupler is drawn to such an extent that, in the waist region, the core of each fiber is effectively lost and the cladding may reach a diameter near that of the former core. The cladding becomes a new "core," and the evanescent field of the propagating light is forced outside this new core, where it envelops both fibers simultaneously and produces the energy exchange between the fibers. A detailed description and analysis of the biconical fused tapered coupler has been given by J. Bures et al. in an article entitled "Analyse d'un coupleur Bidirectional a Fibres Optiques Monomodes Fusionnes", Applied Optics (Journal of the Optical Society of America), Vol. 22, No. 12, Jun. 15, 1983, pp. 1918–1922.

Biconical fused tapered couplers have the advantageous property that the output ratio can be changed by bending the fusion region. Because the output ratio changes in accordance with the amount of bending, such couplers can be used in virtually any sensing application involving motion that can be coupled to the fusion region.

Because variable coupler fiberoptic sensors can be made entirely from dielectric materials and optically coupled to remote electronics, they are particularly advantageous for applications in which the presence of electrically conductive elements at the sensor location would pose the risk of electrical shock, burns, fire, or explosion. In the medical field, for example, variable coupler fiberoptic sensors have been proposed for monitoring patient heartbeat during MRI examinations. See U.S. Pat. No. 5,074,309 to Gerdt, which discloses the use of such sensors for monitoring cardiovascular sounds including both audible and sub-audible sounds from the heart, pulse, and circulatory system of a patient. Other applications of variable coupler fiberoptic sensors can be found in U.S. Pat. No. 4,634,858 to Gerdt et al. (disclosing application to accelerometers), U.S. Pat. No. 5,671,191 to Gerdt (disclosing application to hydrophones), and elsewhere in the art.

Conventional variable coupler fiberoptic sensors have relied upon designs in which the fiberoptic coupler is pulled straight, secured under tension to a plastic support member and, in the resulting pre-tensioned linear (straight) form, encapsulated in an elastomeric material such as silicone rubber. The encapsulant forms a sensing membrane that can be deflected by external forces to cause bending of the coupler in the fusion region. The bending of the fusion region results in measurable changes in the output ratio of the coupler. The displacement of the membrane can be made sensitive to as little as one micron of movement with a range of several millimeters.

Figure 23:
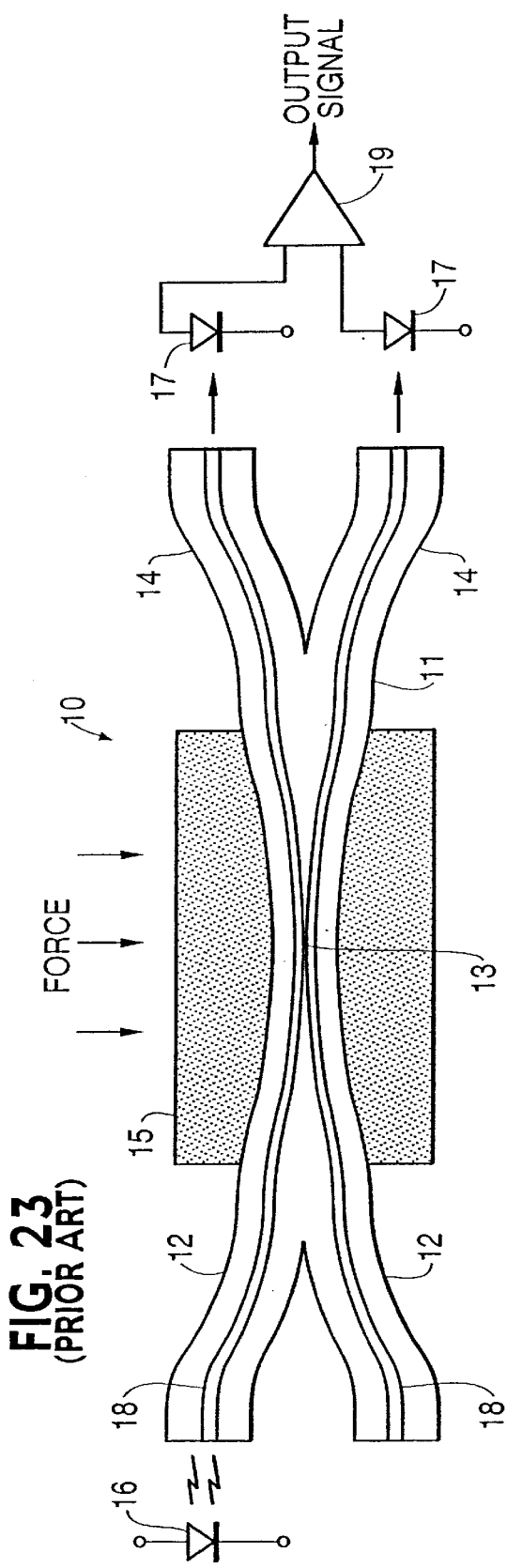
FIG. 23 illustrates the basic construction of a conventional variable coupler fiberoptic sensor.

FIG. 23 of the accompanying drawings illustrates the basic principles of a sensing apparatus including a variable coupler fiberoptic sensor 10 as described above. In the form shown, the sensor 10 includes a 2×2 biconical fused tapered coupler 11 produced by drawing and fusing two optical fibers to form the waist or fusion region 13. Portions of the original fibers merging into one end of the fusion region become input fibers 12 of the sensor, whereas portions of the original fibers emerging from the opposite end of the fusion region become output fibers 14 of the sensor. Reference numbers 18 denote the optical fiber cores. The fusion region 13 is encapsulated in an elastomeric medium 15, which constitutes the sensing membrane. The support member is not shown in FIG. 1.

In practice, one of the input fibers 12 is illuminated by a source of optical energy 16, which may be an LED or a semiconductor laser, for example. The optical energy is divided by the coupler 11 and coupled to output fibers 14 in a ratio that changes in accordance with the amount of bending of the fusion region as a result of external force exerted on the sensing membrane. The changes in the division of optical energy between output fibers 14 may be measured by two photodetectors 17 which provide electrical inputs to a differential amplifier 19. Thus, the output signal of differential amplifier 19 is representative of the force exerted upon medium 15. It will be appreciated that if only one of the input fibers 12 is used to introduce light into the sensor, the other input fiber may be cut short. Alternatively, it may be retained as a backup in the event of a failure of the primary input fiber. It should be noted that, for simplicity, the coupler 11 is shown without the aforementioned fiber twisting in the fusion region. Such twisting is ordinarily preferred, however, to reduce lead sensitivity, which refers to changing of the output light division in response to movement of the input fiber(s).

Despite their advantages, conventional variable coupler fiberoptic sensors have been subject to certain limitations inherent in the conventional pre-tensioned linear (straight) coupler design. The conventional design imposes, among other things, significant geometrical limitations. In particular, the size of the sensor must be sufficient to accommodate the fiberoptic leads at both ends of the sensor. The fiberoptic lead arrangement also requires the presence of a clear space around both ends of the sensor in use. Especially in medical applications, such as when placing a sensor on a patient's body for continuous monitoring, the size and lead positions of the sensor are both important issues. Another limitation results from the fact that any displacement of the fusion region necessarily places it under increased tension. At some point of displacement, the tension in the fusion region will become excessive, causing the fusion region to crack or break, with resulting failure of the coupler.

Returning to the invention, the apparatus of FIG. 3 utilizes an improved variable coupler fiberoptic sensor designed to overcome one or more disadvantages of the conventional pre-tensioned linear sensor design. More particularly, the sensor used in the present apparatus may have an improved design that permits deflection of the coupler fusion region without accompanying tension. The coupler fusion region is preferably arranged substantially in a U-shape, but may more generally be configured as disclosed in co-pending U.S. application Ser. No. 09/316,143 filed May 21, 1999, which is incorporated herein by reference. With a substantially U-shaped configuration it becomes possible to locate the fiberoptic leads of the sensor adjacent to each other, rather than at opposite ends of the sensor, thus avoiding the earlier discussed geometrical limitations inherent in the conventional pre-tensioned linear coupler design.

It will be appreciated that by using two such sensors, the apparatus of FIG. 3 fully realizes the benefit of the improved sensor design. It is permissible within the broader scope of the invention, however, to use one such sensor in combination with another pulse sensor that does not utilize the improved design described above, such as a conventional linear variable coupler fiberoptic sensor or even a piezoelectric sensor.

As shown in FIG. 3, each of the sensors S1',S2' is coupled to a corresponding light source 40 (e.g., a laser) and a corresponding photodetector/differential amplifier circuit 42 as previously described. These circuits have respective outputs connected to corresponding inputs of a digital signal processor (DSP) 44, each through an analog-to-digital converter 43. The digital signal processor processes the input signals to detect the pulse transit time.

It is possible to combine the sensors S1', S2' by arranging their respective fiberoptic components in mutual proximity on a common support structure. But, as earlier noted, locating the pulse sensors in mutual proximity leaves little margin for error because the measured pulse transit time will be short.

The digital signal processor 44 may be programmed to determine the pulse transit time in any desired manner, including but not limited to the manner explained in connection with FIG. 2.

Figure 4:
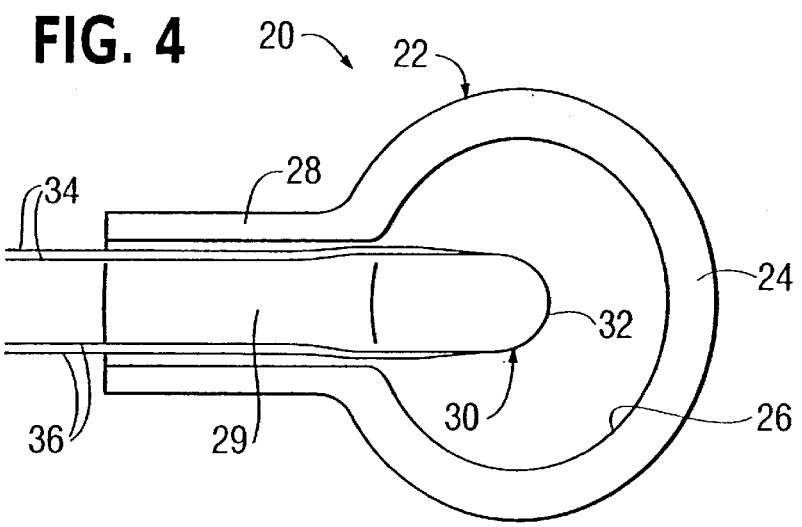
FIG. 4 is a top view of a variable coupler fiberoptic sensor useful in the apparatus of FIGS. 1 and 3.
Figure 5:
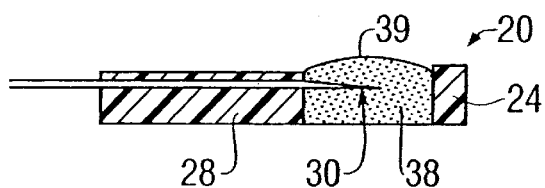
FIG. 5 is a sectional side view of the sensor of FIG. 4.

FIGS. 4 and 5 of the accompanying drawings show a specific example of an improved variable coupler fiberoptic sensor 20 useful in the apparatus of the present invention. The sensor is constructed for placement against a person's body, such as on the chest, arm, or wrist, for sensing skin displacements due to the pulse. The sensor is more generally capable of sensing both audible and sub-audible cardiovascular and breathing sounds that are manifested by skin displacement.

The sensor 20 comprises a support member 22 having a generally circular head portion 24, which is provided with a central well or through hole 26, and a handle-like extension 28. A biconical fused tapered coupler 30 is mounted to the support member with at least a portion (here, the entirety) of its fused coupling region 32 disposed in the space 26 and arranged in a U-shape. Input fiber leads 34 and output fiber leads 36 of the coupler are disposed beside one another in a channel 29 formed in the extension 28. The leads are manipulated so as to bend the coupling region 32 through 180° into the desired shape and then secured within the channel by a suitable adhesive, such as an epoxy-based glue. The coupling region, which is not under tension, may be potted by filling the space 26 with elastomer to form a sensing membrane 38 (not shown in FIG. 4) in the known manner—for example, by filling with a silicone rubber such as GE RTV 12. Alternatively, as will be seen hereinafter, the coupling region may be coated with a layer of coating material such as GE SS 4004 (polydimethylsiloxane with methyl silsesquioxanes) to eliminate the need for potting. This material is normally used as a primer for bonding room temperature vulcanizing (RTV) materials to surfaces that would otherwise form weak bonds. The advantage of eliminating the potting is that the sensitivity is increased, because the potting tends to reduce sensitivity no matter how thinly it is applied. Support member 22 is suitably formed of a moldable plastic, such as Plexiglass®, polyvinyl chloride (PVC), or other suitable materials known in the art.

As shown in FIG. 5, the upper portion of the membrane 38 has a convex surface 39 that protrudes from the plane of the support structure for contacting a person's body. The convex configuration of the contact surface makes the sensor more of a point probe to better localize the cardiovascular sounds being monitored. In a practical embodiment of the sensor, the maximum diameter of the membrane may be about the same as that of a nickel coin with the contact surface protruding by about half that amount, but the membrane may be smaller or larger as desired to suit a particular application. The support plate dimensions may be any convenient size, so long as the coupler fusion region and the fiber portions near the fusion region are securely supported. The sensitivity of the device is dependent upon the stiffness of the membrane, as in prior devices.

When the contact surface 39 is positioned upon a pulse point, such as on a person's arm over the brachial artery or radial artery, the membrane 38 couples skin displacements associated with the pulse to the coupling region 32 of the fiberoptic coupler 30. The coupling region is thereby deflected, changing the light output ratio of the output fibers 36 in accordance with the sounds being monitored.

Figure 6:
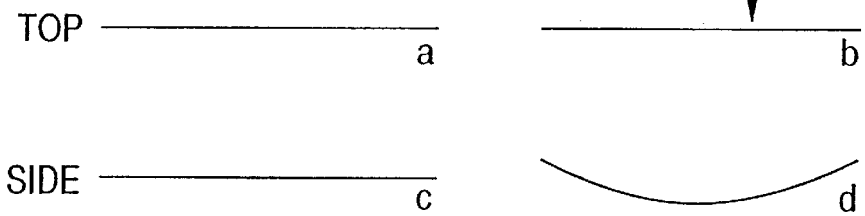
FIG. 6 shows explanatory views (Views 6a–6d) of normal and deflected states of the fusion region of a conventional pre-tensioned linear coupler.
Figure 7:
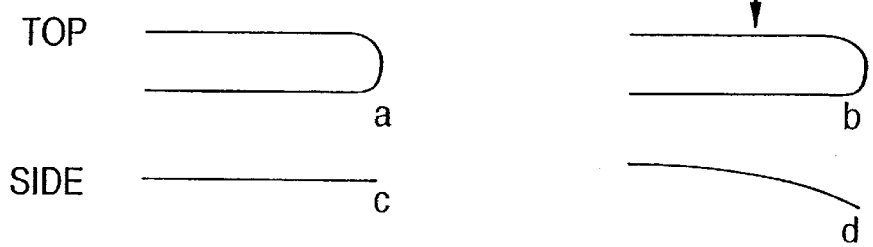
FIG. 7 shows corresponding explanatory views (Views 7a–7d) for a U-shaped fusion region.

FIGS. 6 and 7 provide a pictorial comparison between the deflection of a conventional pre-tensioned linear fiberoptic coupler and the deflection of the U-shaped coupler in the sensor of FIGS. 4 and 5. Views 6a and 6c are top and side views, respectively, showing the fusion region of the conventional coupler in its normal state. Views 6b and 6d are corresponding views of the fusion region being deflected by a downward force F. Views 7a–7d in FIG. 7 are corresponding views to FIG. 6, but show the U-shaped coupler employed in the present invention.

Figure 8:
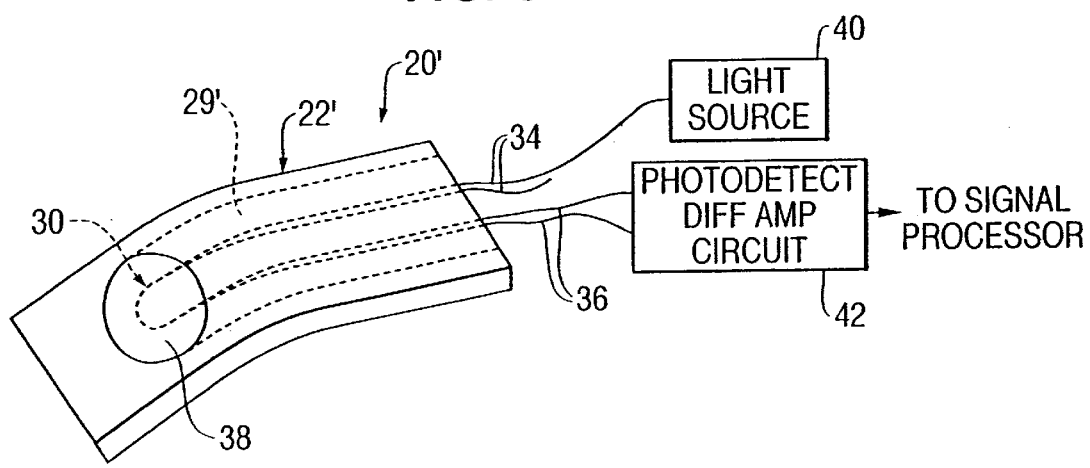
FIG. 8 shows a variable coupler fiberoptic sensor useful in apparatus according to the invention.

As will be appreciated from View 7d, the deflection of the fusion region in the conventional coupler causes a bowing that tends to stretch and thereby increase the tension on the fusion region. By contrast, the deflection of the U-shaped fusion region in View 7d, which is seen to occur along a direction perpendicular to the plane of the U-shape, merely causes a flexing of the U along its height (horizontal dimension in View 7d), without subjecting the fusion region to tension. Thus, even large displacements of the fusion will not cause cracking or breaking. FIG. 8 shows another variable coupler fiberoptic sensor 20' that may be used in the apparatus of the invention. The sensor has the same basic structure as that of the previous embodiment, except that the support member 22' is formed as a substantially rectangular plate angled at about 30° to conform to the human arm/wrist anatomy and facilitate wearing of the sensor by the patient, as by strapping the sensor to the arm/wrist. If appropriate to a particular application, the support member may house the light source 40, the photodetection/differential amplifier circuit 42, and a radio transmitting device (not shown) coupled to the circuit 42 to provide for remote monitoring. Indeed, such provision can be made in any of the sensor structures described herein.

Figure 9:
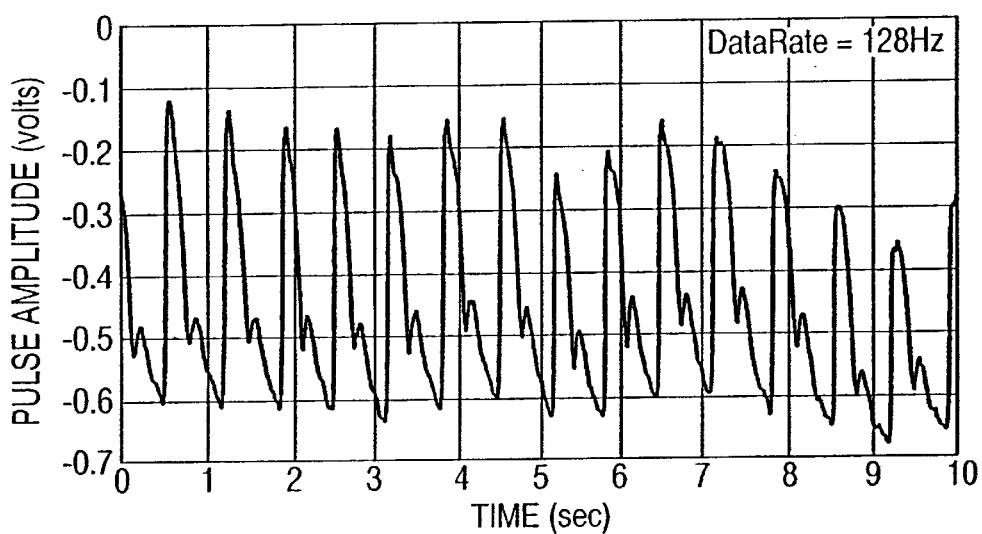
FIG. 9 is a graph depicting the response of the sensor of FIG. 8 to pulsations of the wrist.

FIG. 9 shows the wrist heartbeat/breathing signal obtained from a human subject with the sensor 20' of FIG. 8. The data stream in FIG. 9 was obtained at a sampling rate of 128 samples per second. It will be appreciated that the pulse waveform, as read by the sensor, is a more complex phenomenon than standard pulse readings. The pulse waveform exhibits the amplitude structure of the pulse as a function of time. The amplitude structure of the pulse is not what is "felt" as an impulse function by a finger at a pulse point, although that function is present. Within the amplitude structure, there are all of the heart sounds as well as information on breathing and other indicators of physical condition. The sensitivity achieved with the improved sensors described herein makes them very good at sensing the complex pulse waveform.

Figure 10:
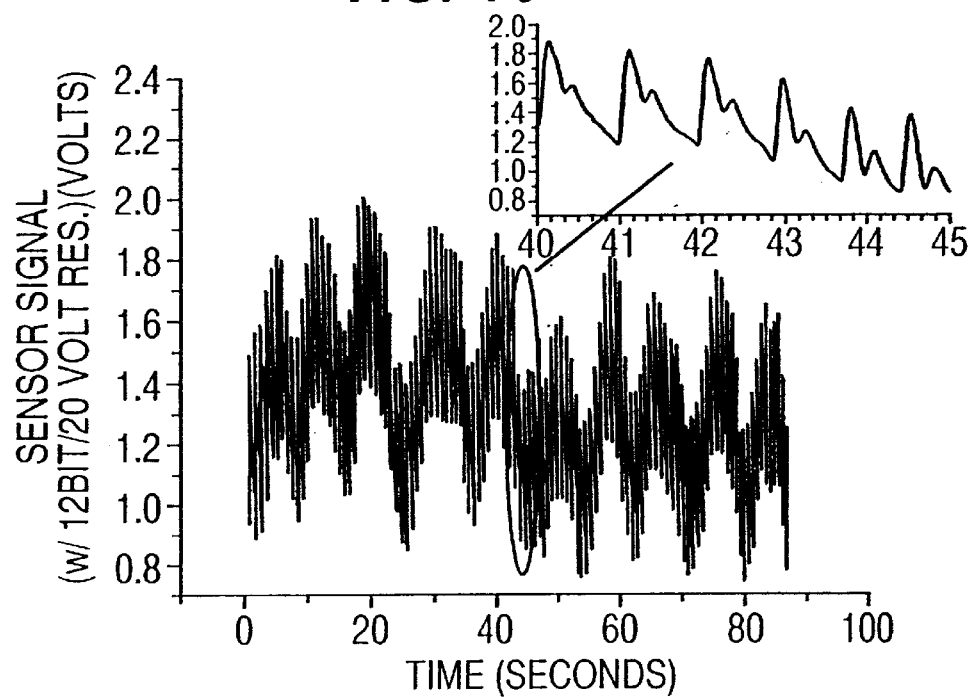
FIG. 10 is another graph of the sensor response at the wrist.

FIG. 10 shows another wrist heartbeat/breathing signal obtained from a human subject with the sensor 20'. Here, the data stream was digitized using a 12-bit A/D converter at a sampling rate of 64 samples per second. The heartbeat signal is very well resolved, as the inset graph demonstrates. In addition, the modulation introduced by the breathing cycle is clearly visible over the course of the 84 second run.

FIGS. 11 and 12 show another arm/wrist sensor 50 that may be used in the apparatus of the invention. In this sensor, the fusion region 62 of the fiberoptic coupler is not potted, but coated as previously discussed. The fusion region 62 is coupled to pulsations of the arm/wrist (denoted by arrow P) by a fluid- or gel-filled elastic pillow 68. The fiberoptic coupler is mounted to a support plate 52 similar to that of FIG. 8, except that the support plate 52 is planar, not angled (the channel for the input and output leads 64, 66 having been omitted from illustration for simplicity). The support plate is secured to the top side of pillow 68 and a cover 69 is attached to the top side of the support plate to protect the fusion region 62 of the coupler 60 at the hole 56. The hole 56 allows the hydraulic pressure of the pulse activity to push on and deflect the fusion region by virtue of the contact between the fusion region and the upper surface of the pillow 68 which, due to its flexibility, protrudes into the hole 56 to contact the coupler fusion region. A strap 57 attached to the support plate 52, as by glue, allows the sensor to be secured to the arm/wrist. Reference numbers 64 and 66 denote the input fibers and output fibers, respectively.

The unpotted sensor design of FIGS. 11 and 12 is advantageous over the potted designs previously described, because the absence of the sensing membrane results in greater sensitivity. Also, unlike the bent design in FIG. 8, the planar configuration of the support plate does not require out-of-plane bending of the coupler leads, which causes a reduction of light intensity. Instead, the coupler is maintained in a planar configuration, which optimizes the light intensity in the system.

Figure 13:
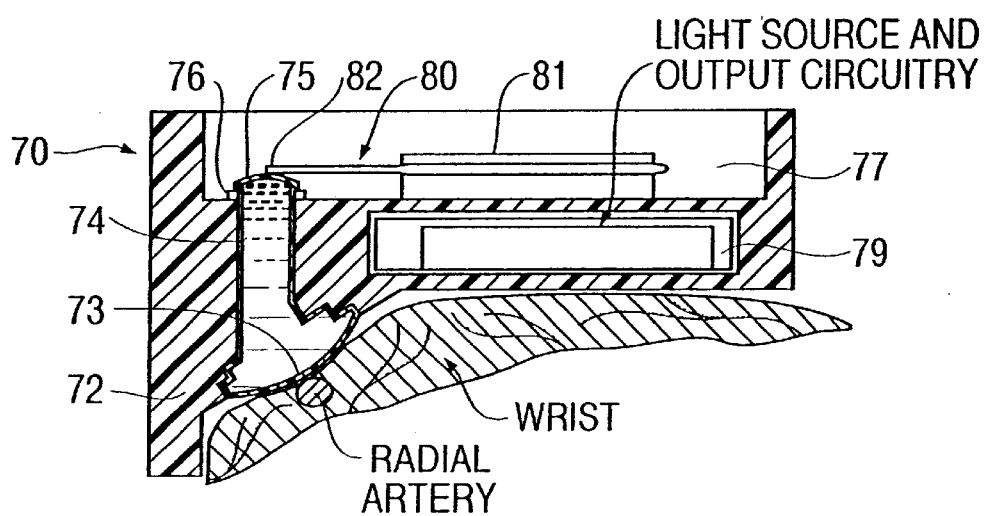
FIG. 13 illustrates another variable coupler fiberoptic sensor useful in apparatus according to the invention, shown in section as worn on the wrist.

FIG. 13 shows still another sensor 70 that may be used in the apparatus of the invention, the sensor being shown in cross-section as worn on the wrist. The sensor includes a frame member 72 having an inner configuration which conforms generally to the wrist, as shown. The frame member may be constructed from any suitable material, preferably a plastic such as Delrin®, PVC, acrylic, Lucite®, Plexiglass®, styrene, or other polymers.

An upper portion of the frame provides a chamber 77 for housing the fiberoptic coupler 80 and its support plate 81. Since the coupler is housed by the frame member, the support plate, which is channeled to receive the input and output leads, need not include an opening (e.g., a well or through hole) to house the fusion region 82 of the coupler as in earlier discussed sensors. The fusion region is coated, rather than potted, as previously described. The support plate 81, which may be of the same material as the frame 72, and the coupler are assembled as a module and glued in place in the chamber 77. The chamber is closed by a protective cover plate (not shown).

To couple the fusion region to the pulsations of the radial artery, a fluid column 74 is provided. The column has a pair of resilient membranes 73 and 75 provided at its inner and outer ends, respectively, and extends through the thickness of the frame 72 between the chamber 77 and the frame inner surface. The coupler module is installed with the coupler fusion region 82 in contact with the outer membrane 75 of the fluid column. The outer membrane is attached to an annular boss 76 to raise the height of the fluid column for contact with the coupler fusion region. The contact with the outer membrane may subject the fusion region to a slight pre-load. The coupler may be manufactured such that the pre-loading of the fusion region will produce a substantially equal division of light between the output fibers, thus providing a more linear dynamic range. The inner portion (lower portion in FIG. 13) of the fluid column is stepped as shown, so as to increase the diameter of the coupling area at the wrist.

The membranes constitute an important part of the fluid column. Since the arterial pulsations are weak, the membranes should be light, thin, and of low durometer and high extensibility for optimum performance. At the same time, at least the inner membrane should be rugged enough to endure continuous contact with the skin. A material found to have excellent characteristics for the membrane is FlexChem, an FDA-approved, highly durable, vinyl based material available in pellet form from Colorite. FlexChem is also thermomoldable, which permits the inner sensing membrane 73 to be molded to provide maximum coupling area with the radial artery and to protrude from the inner surface of the frame member 72 for better coupling with the wrist. A compatible fluid for use with FlexChem membranes is medical grade MDM silicone fluid available from Applied Silicone Corp. Water, incidentally, is not preferred for use with FlexChem membranes since the membranes are permeable to water vapor.

Several inner membrane sizes were tested to determine the effect on sensor response. In particular, membrane diameters of 4 mm, 7 mm, and 10 mm were tested for response to driven-oscillator stimuli calibrated using a commercial accelerometer. The response was examined over a frequency range of 0 to about 11 Hz (cardiovascular and breathing signals are typically in the range from 0.1 to 4 Hz). Each of the membranes provided acceptable response, with the 10 mm membrane providing the best response.

Returning to FIG. 13, the present construction also demonstrates how ancillary components, such as the light source and output circuitry (e.g., photodetectors and differential amplifier circuitry) may be incorporated into the sensor unit. More particularly, such components may be housed in one (as shown) or more internal chambers 79 of the frame 72.

Figure 16:
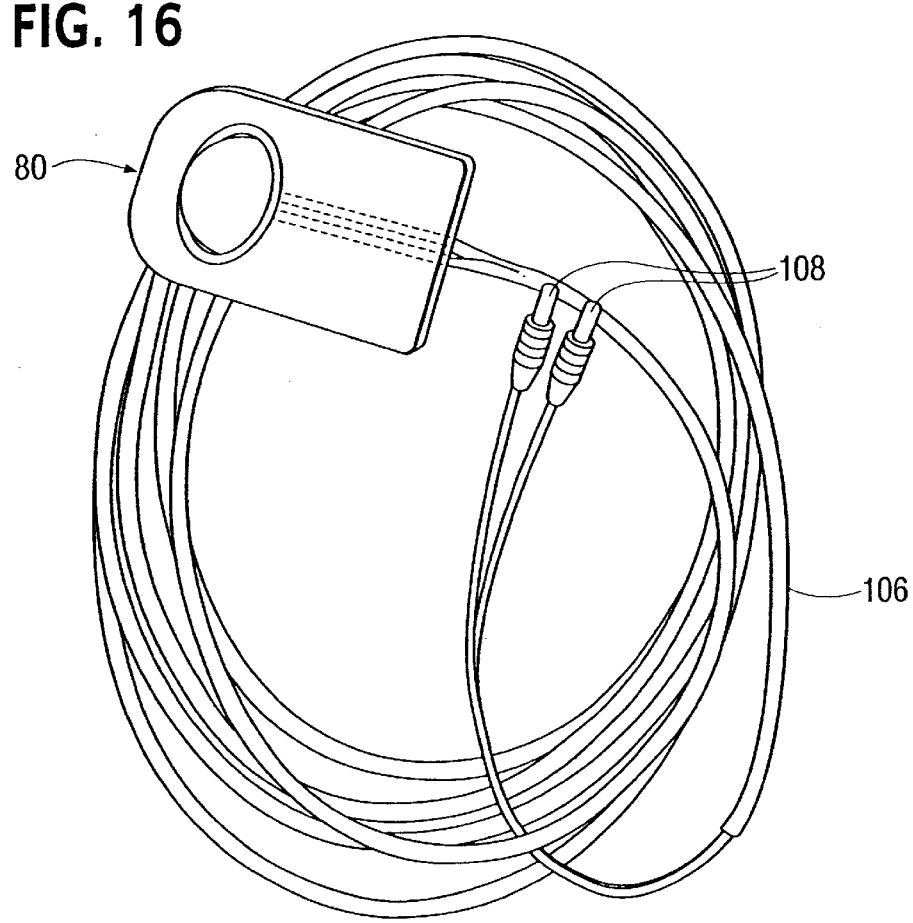
FIG. 16 is a perspective view showing the FIG. 14 sensor and its fiberoptic leads with installed connectors.
Figure 14:
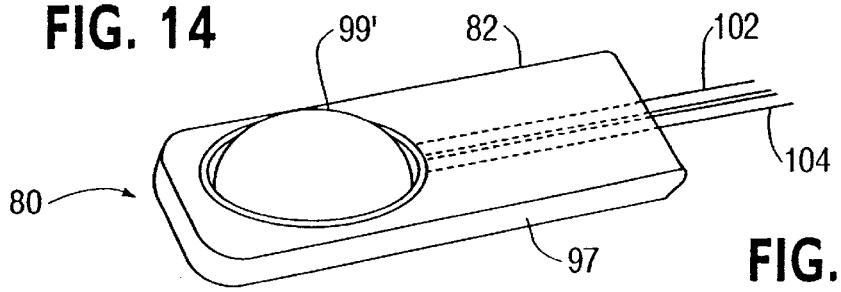
FIG. 14 is a perspective view of a carotid artery sensor useful in apparatus according to the invention.
Figure 15:
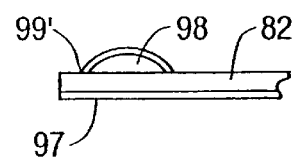
FIG. 15 is a fragmentary side elevation of the FIG. 14 sensor.

FIGS. 14–16 illustrate another sensor 80, designed for application to the carotid artery. This sensor uses a planar, channeled support plate 82 and coupler arrangement similar to that of FIG. 11, except that the fusion region is potted to provide a sensor membrane. The membrane area may be made sufficiently large (e.g., about the size of a quarter dollar) to allow for the addition of a spherical cap 99' over the convexly protruding surface of the sensing membrane 98. The addition of the spherical cap renders the sensor less sensitive to any rocking motion caused by the hand when the sensor is manually pressed against the neck. The coupler is protected at the back side (bottom in FIGS. 14 and 15) of the sensor by a plastic cover plate 97. The sensor may be secured to the neck by any suitable means, such as adhesive tape.

The input and output fibers are encased as pairs in respective protective sheaths 102 and 104, which in turn are encased in an outer protective sheath 106. Fiberoptic connectors 108 are provided at the ends of the leads to interface the sensor with external components.

FIGS. 17–21 are plots showing brachial and radial artery pulse waveforms and corresponding pulse transit times obtained with an apparatus according to FIG. 3 using two variable coupler fiberoptic sensors of the improved type described herein. The digital signal processor was programmed in accordance with the method described in connection with FIG. 2. It will be appreciated, incidentally, that the apparatus of FIGS. 1 and 3 are not mutually exclusive. For example, when programmed in accordance with FIG. 2, the apparatus of FIG. 3 will constitute a particular form of the structure generally represented in FIG. 1. Conversely, when provided with an improved variable coupler fiberoptic sensor of the type described, the apparatus of FIG. 1 will constitute a particular form of the structure generally represented in FIG. 3.

Figure 17:
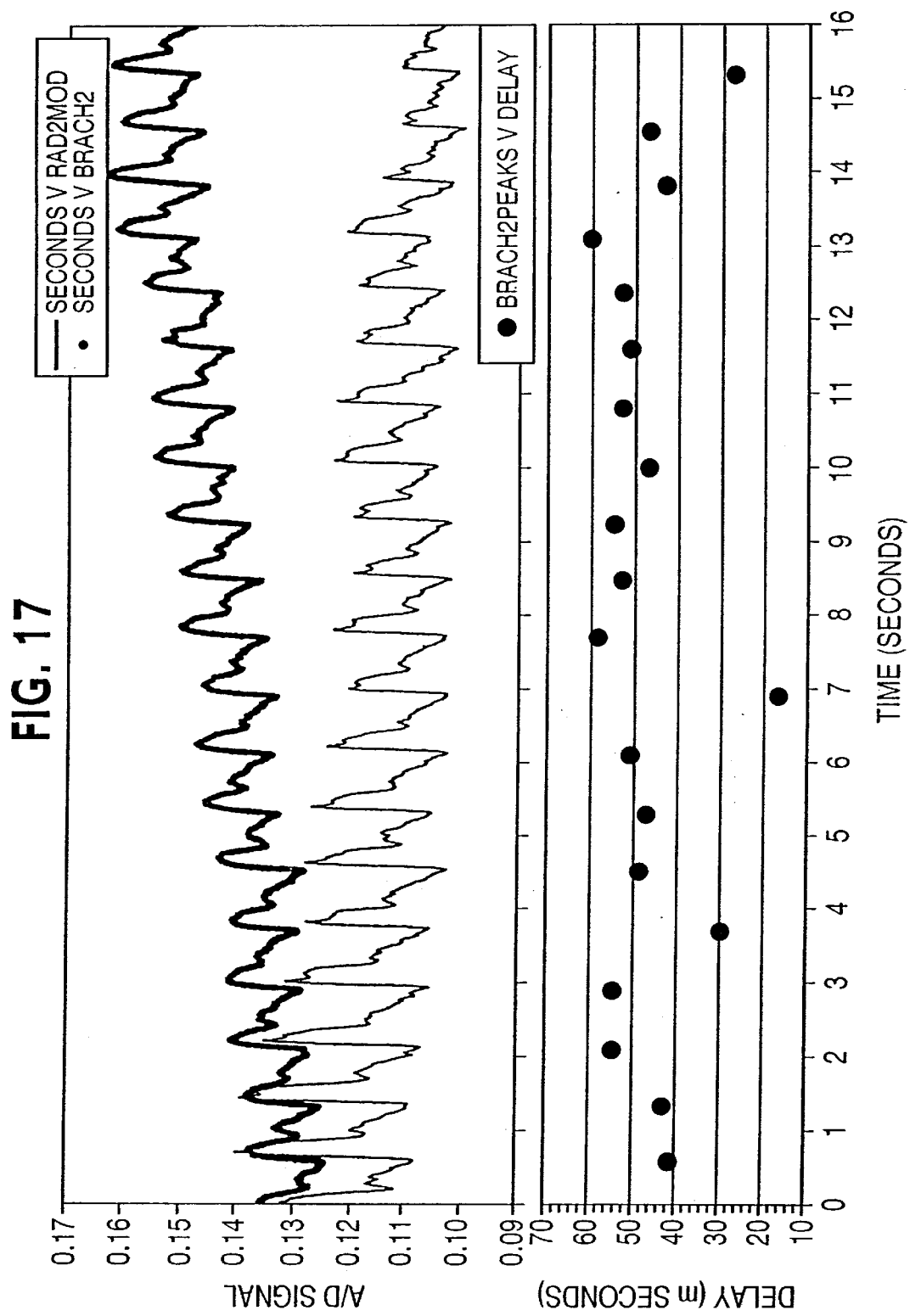
FIGS. 17–21 are plots showing pulse waveforms and corresponding pulse transit times obtained using an apparatus as shown in FIG. 3 performing the method shown in FIG. 2.

FIG. 17 shows data for a supine adult male breathing normally. The pulse transit time is seen run about 50 msec. on average.

Figure 18:
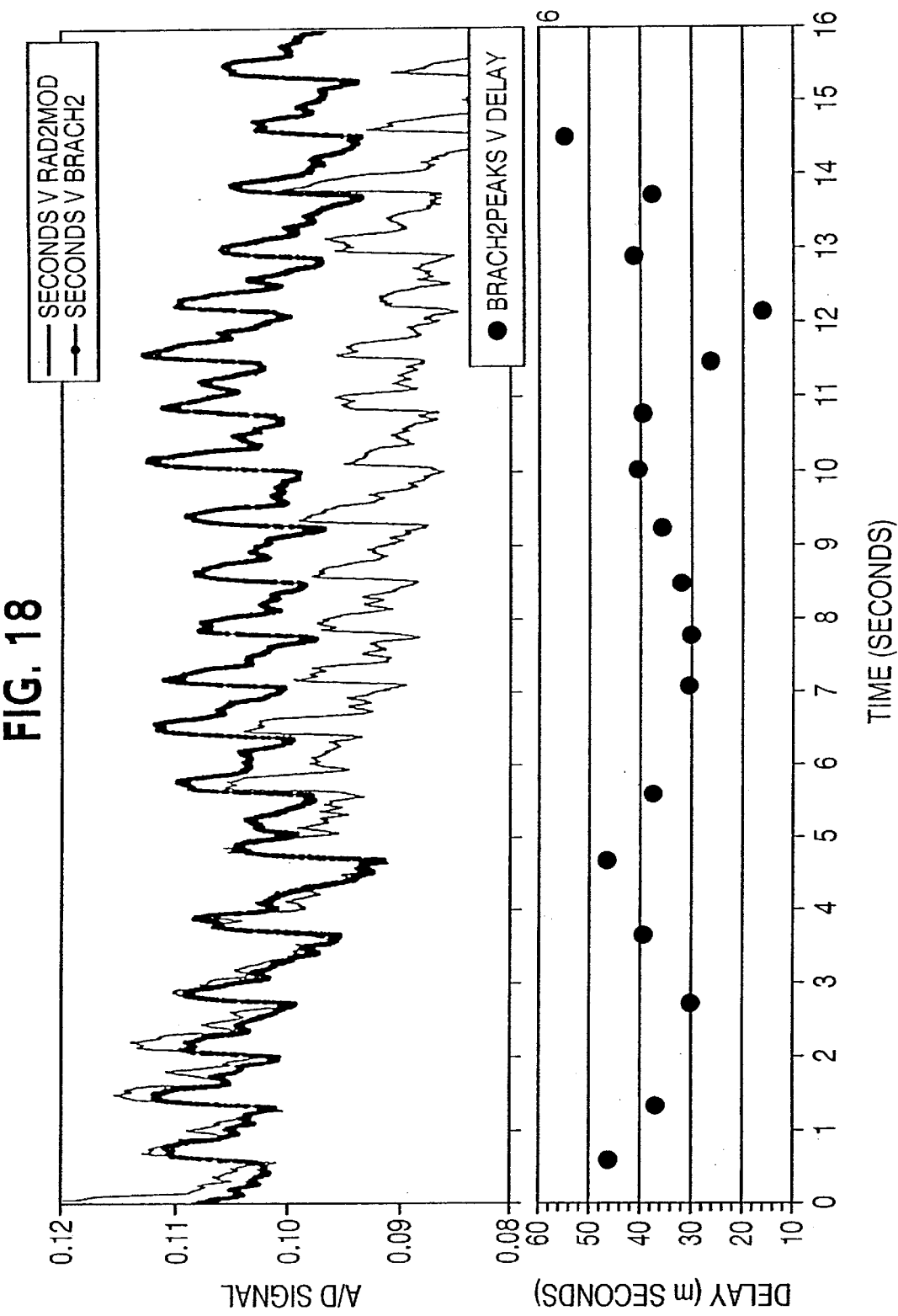

FIG. 18 is a similar plot except that the breathing pattern was changed to simulate sleep, inhaling for two seconds and exhaling for 3 seconds. The pulse transit time runs about 35 msec. on average.

Figure 19:
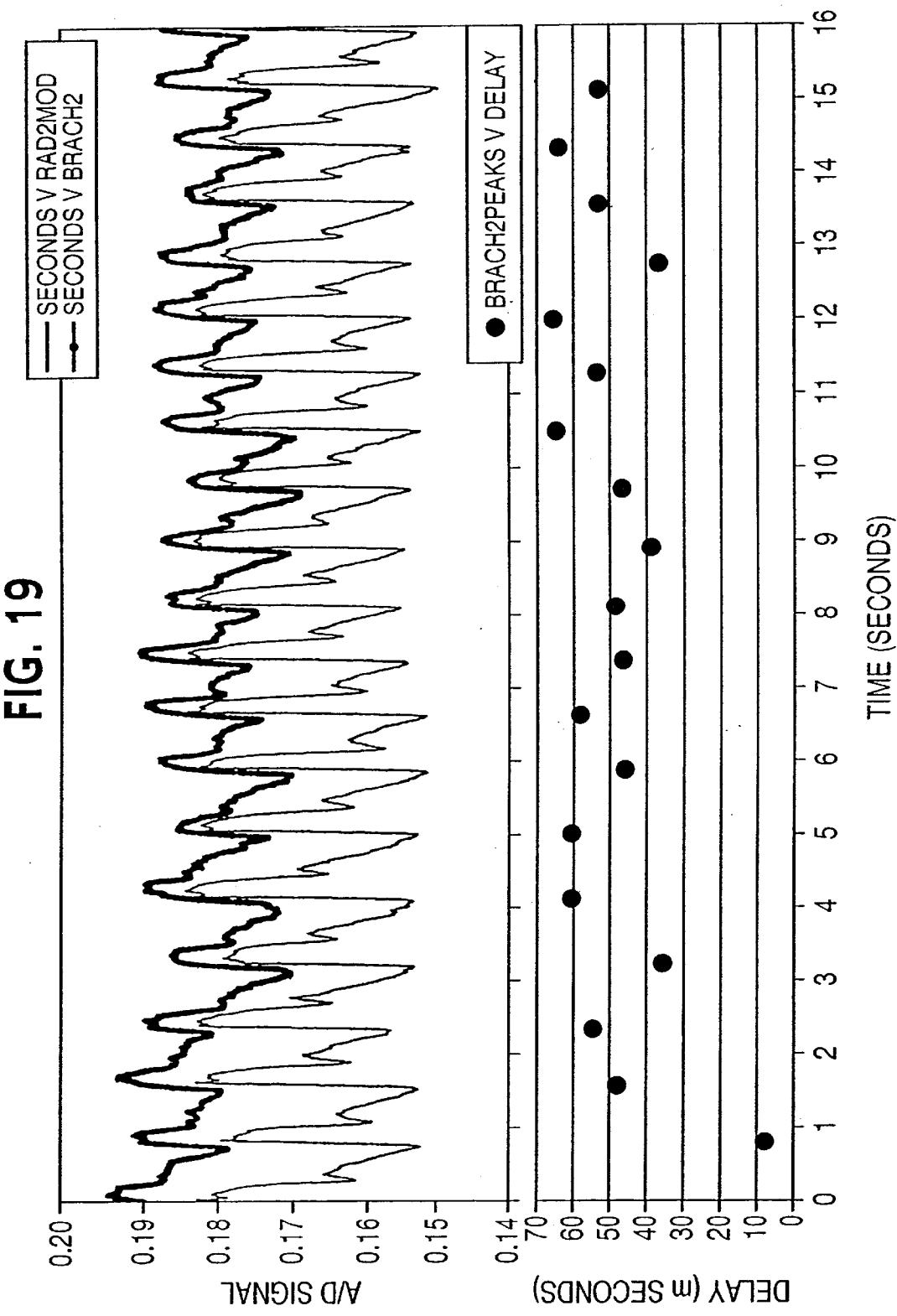
Figure 20:
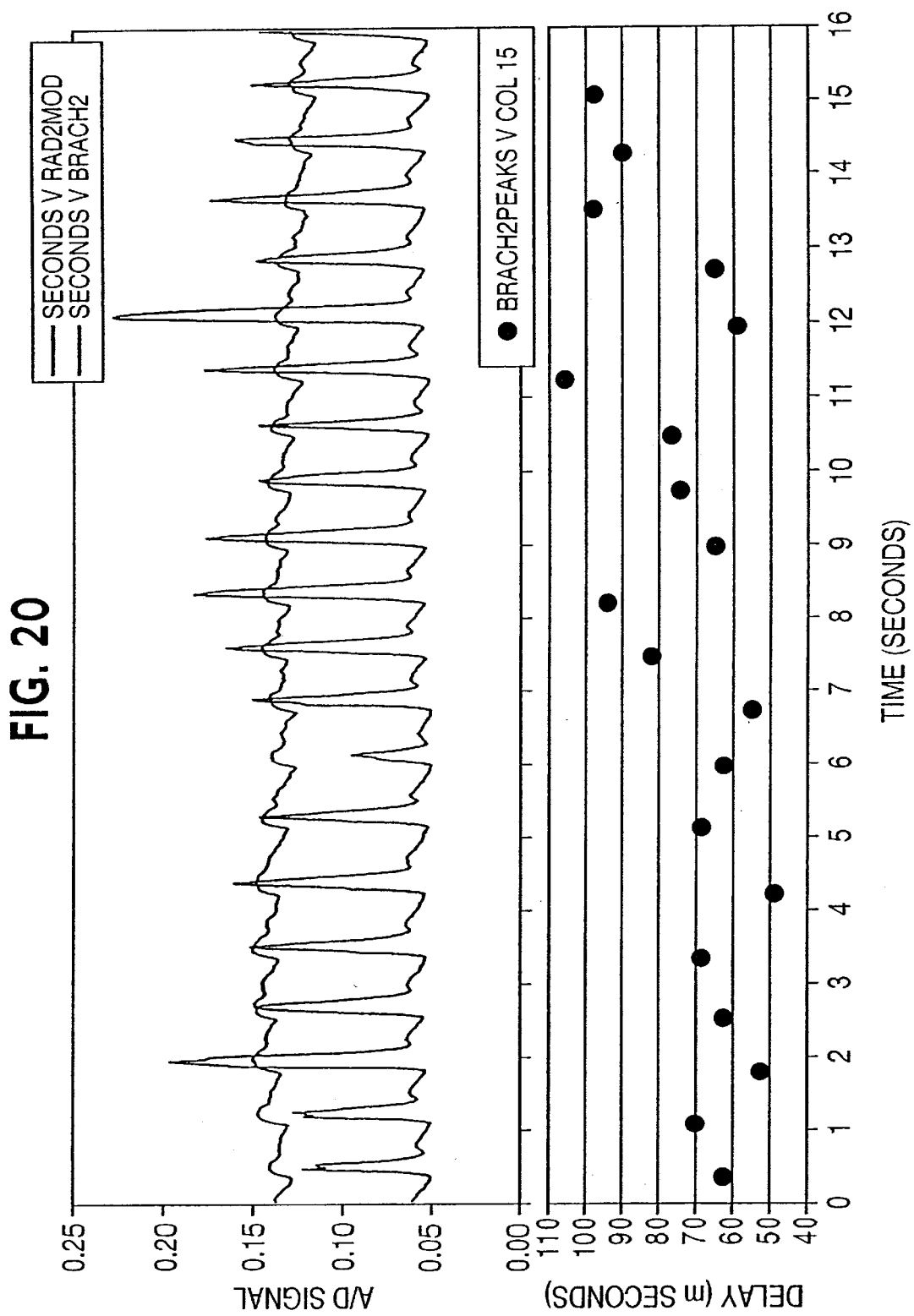

FIG. 19 used a similar breathing pattern as just described, but breathing was constricted by pinching the nose. Blood pressure falls under these circumstances since the thoracic cavity is under more negative pressure (pulsus paradoxus). This is evidenced by the increase in pulse transit time to about 50 msec. on average.

FIG. 20 again used a similar breathing pattern, but with complete obstruction of airflow. To simulate an apnea event, no air was admitted to the lungs over the entire 16 sec. test period. As is apparent, the pulse transit time increased substantially, indicating a further fall in blood pressure relative to FIG. 19.

Figure 21:
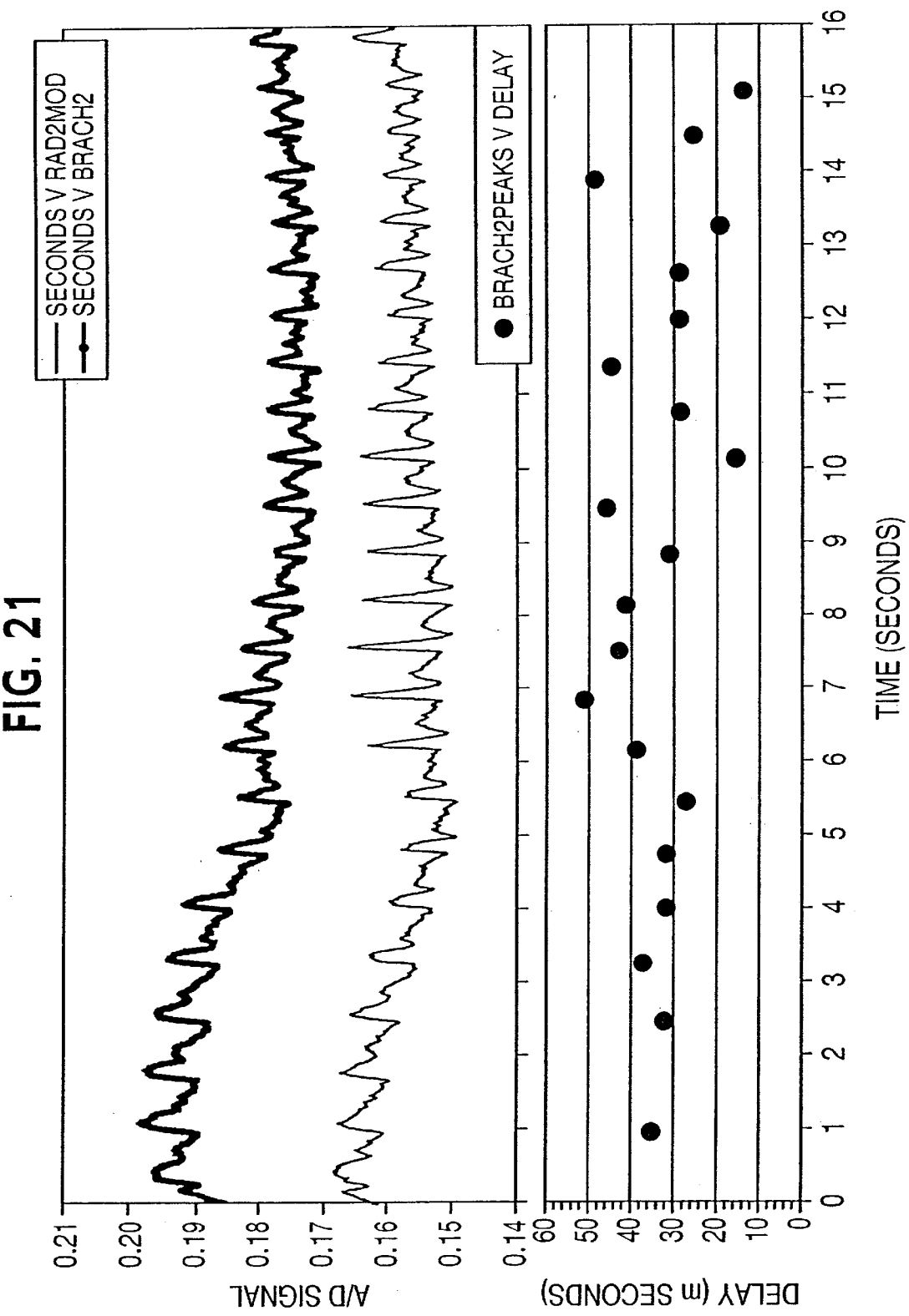
Figure 22:
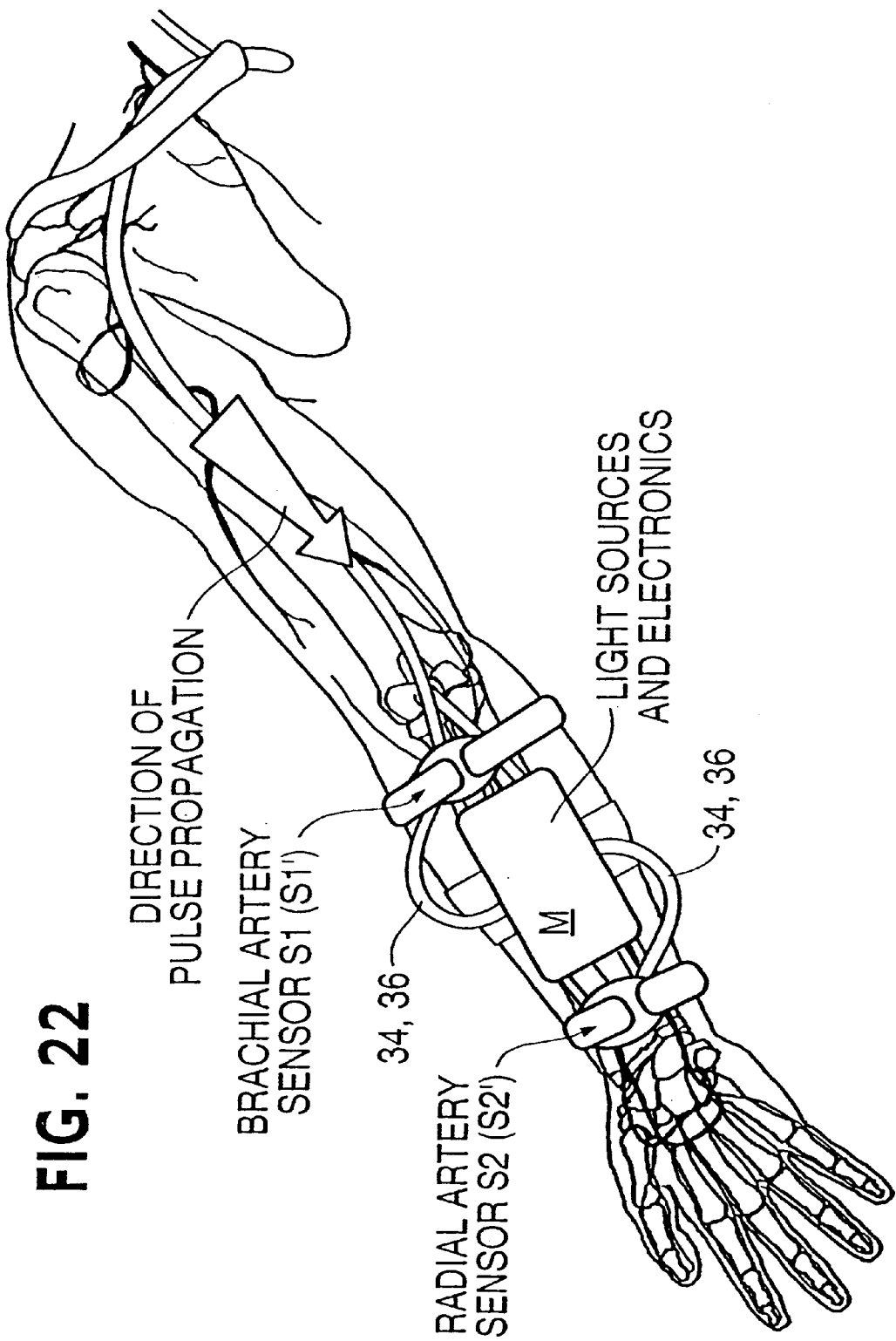
FIG. 22 is a diagram illustrating a practical arrangement of an apparatus according to FIG. 1 or FIG. 3.

FIG. 21 shows another plot for a 16 sec. period of no breathing, but with a full lung. The pulse transit time values decreased to about 30 msec. on average, indicating higher blood pressure.

The results of FIGS. 17–21 are consistent with the known fact that negative lung pressure causes blood pressure to fall whereas increasingly positive lung pressure causes blood pressure to rise.

FIG. 23 depicts a practical arrangement using variable coupler fiberoptic sensors for implementing an apparatus according to FIG. 1 or FIG. 3. In the form shown, the sensors S1,S2 (S1',S2') are strapped to the arm over brachial and radial artery pulse points, respectively. The light sources and signal processing electronics are contained in a module M also strapped to the arm. The sensors and the module M are connected through corresponding sets of fiberoptic leads 34,36. The module M may include a radio transmitting device (not shown) to communicate with external electronics.

It should be noted that the optical fiber used in the above-described sensors is most preferably of very high quality, such as Corning SMF28 which exhibits an optical loss of about 0.18 dB per Km. The photodetectors may be gallium-aluminum-arsenide or germanium detectors for light wavelengths above 900 nm and silicon detectors for shorter wavelengths.

The photodetectors may be connected in either a photovoltaic mode or a photoconductive mode. In the photovoltaic mode, transimpedance amplifiers (which convert current to voltage) may be used to couple the detectors to the differential amplifier inputs. The transimpedance amplifier outputs may also be filtered to eliminate broadband noise. In the photoconductive mode, the detector outputs can be connected to a conventional voltage amplifier. This approach results in more noise, but may be used in applications where cost is a major concern and a lower noise level is not.

It is to be understood, of course, that the foregoing embodiments of the invention are merely illustrative and that numerous variations of the invention are possible in keeping with the invention as more broadly described herein.

What is claimed is:

1. A method of measuring pulse transit time of a living subject, comprising:
producing first and second pulse wave signals by sensing the pulse at first and second pulse points, respectively, said first and second pulse points being spaced from one another;
differentiating said first and second pulse wave signals;
selecting corresponding points of said first and second pulse wave signals based on results of said differentiating; and
detecting a time delay between the selected points.

2. A method according to claim 1, wherein said selecting includes selecting a point of predetermined slope characteristic from each of said first and second pulse wave signals.

3. A method according to claim 2, wherein said selecting includes selecting a point of maximum slope from each of said first and second pulse wave signals.

4. A method according to claim 1, wherein said first and second pulse points are located on a first artery and a second artery, respectively.

5. A method according to claim 4, wherein said first artery is a brachial artery and said second artery is a radial artery.

6. A method according to claim 1, wherein the pulse at at least one of said first and second pulse points is sensed with a fiberoptic sensor having a fused-fiber coupling region.

7. A method according to claim 6, wherein at least a portion of said fused-fiber coupling region is configured such that it can be deflected to change an output of said fiberoptic sensor without said coupling region being put under tension.

8. A method according to claim 6, wherein said fused-fiber coupling region is substantially U-shaped.

9. An apparatus that measures pulse transit time of a living subject, comprising:
first and second pulse sensors to be placed at a first pulse point and a second pulse point, respectively, said first pulse point and said second pulse point being spaced from one another;
at least one of said first and second sensors being a fiberoptic sensor including a fused-fiber coupling region having at least a portion constructed such that it can be deflected without said coupling region being put under tension; and
a signal processing unit connected to said first and second pulse sensors and operative to determine pulse transit time based on outputs of said first and second sensors.

10. An apparatus according to claim 9, wherein each of said first and second sensors is a fiberoptic sensor having a fused-fiber coupling region with a portion configured as aforesaid.

11. An apparatus according to claim 9, further comprising an electro-optic circuit optically coupled to a plurality of output optical fibers of said one sensor to convert light received from said output fibers to an electrical output having a level dependent upon an amount of deflection of said portion of said coupling region.

12. An apparatus according to claim 11, wherein said electro-optic circuit comprises a plurality of photodetectors optically coupled to said plurality of output fibers, respectively, and a differential amplifier circuit to which outputs of said photodetectors are connected.

13. An apparatus according to claim 9, wherein said one sensor has a support structure configured to conform generally with a portion of a person's arm.

14. An apparatus that measures pulse transit time of a living subject, comprising:
first and second pulse sensors to be placed at a first pulse point and a second pulse point, respectively, said first pulse point and said second pulse point being spaced from one another;
at least one of said sensors being a fiberoptic sensor including a substantially U-shaped, fused-fiber coupling region; and
a signal processing unit connected to said first and second pulse sensors and operative to determine pulse transit time based on outputs of said first and second sensors.

15. An apparatus according to claim 14, wherein each of said first and second sensors is a fiberoptic sensor having a substantially U-shaped, fused-fiber coupling region.

16. An apparatus according to claim 14, further comprising an electro-optic circuit optically coupled to a plurality of output optical fibers of said one sensor to convert light received from said output fibers to an electrical output having a level dependent upon an amount of deflection of said coupling region.

17. An apparatus according to claim 16, wherein said electro-optic circuit comprises a plurality of photodetectors optically coupled to said plurality of output fibers, respectively, and a differential amplifier circuit to which outputs of said photodetectors are connected.

18. An apparatus according to claim 14, wherein said one sensor has a support structure configured to conform generally with a portion of a person's arm.

19. An apparatus that measures pulse transit time of a living subject, comprising:
first and second pulse sensors to be placed at a first pulse point and a second pulse point, respectively, said first pulse point and said second pulse point being spaced from one another; and
a signal processing system connected to said first and second pulse sensors and operative to differentiate first and second pulse wave signals corresponding to outputs of said first and second pulse sensors, respectively, to select corresponding points of said first and second pulse wave signals based on the results of the differentiation, and to detect a time delay between the selected points.

20. An apparatus according to claim 19, wherein said signal processing system selects a point of predetermined slope characteristic from each of said first and second pulse wave signals.

21. An apparatus according to claim 20, wherein said signal processing system selects a point of maximum slope from each of said first and second pulse wave signals.

22. An apparatus according to claim 19, wherein at least one of said pulse sensors is a fiberoptic sensor having a fused-fiber coupling region.

23. An apparatus according to claim 22, wherein at least a portion of said fused-fiber coupling region is configured such that it can be deflected to change an output of said fiberoptic sensor without said coupling region being put under tension.

24. A method according to claim 22, wherein said fused-fiber coupling region is substantially U-shaped.

* * * * *